US012558038B2

(12) United States Patent
Neumann

(10) Patent No.: US 12,558,038 B2
(45) Date of Patent: Feb. 24, 2026

(54) METHODS AND SYSTEMS FOR DETERMINING THE PHYSICAL STATUS OF A SUBJECT

(71) Applicant: KPN INNOVATIONS, LLC., Lakewood, CO (US)

(72) Inventor: Kenneth Neumann, Lakewood, CO (US)

(73) Assignee: KPN INNOVATIONS, LLC., Lakewood, CO (US)

( * ) Notice: Subject to any disclaimer, the term of this patent is extended or adjusted under 35 U.S.C. 154(b) by 666 days.

(21) Appl. No.: 17/106,519

(22) Filed: Nov. 30, 2020

(65) Prior Publication Data

US 2022/0167929 A1    Jun. 2, 2022

(51) Int. Cl.
| | |
|---|---|
| *A61B 5/00* | (2006.01) |
| *A61B 5/11* | (2006.01) |
| *A61B 5/22* | (2006.01) |
| *G06N 20/00* | (2019.01) |
| *G16H 20/30* | (2018.01) |

(Continued)

(52) U.S. Cl.
CPC .......... *A61B 5/7267* (2013.01); *A61B 5/1118* (2013.01); *A61B 5/224* (2013.01); *G06N 20/00* (2019.01); *G16H 20/30* (2018.01); *G16H 40/67* (2018.01); *G16H 50/20* (2018.01); *G16H 50/30* (2018.01)

(58) Field of Classification Search
None
See application file for complete search history.

(56) References Cited

U.S. PATENT DOCUMENTS

| 10,568,570 B1 * | 2/2020 | Sherpa | ................... | G06N 3/084 |
|---|---|---|---|---|
| 10,700,774 B2 * | 6/2020 | Panther | ................ | A61B 5/0002 |

(Continued)

FOREIGN PATENT DOCUMENTS

| TW | 202034345 A * | 9/2020 | ............. | A61B 5/024 |
|---|---|---|---|---|
| WO | WO-2020210487 A1 * | 10/2020 | ............. | G16B 30/10 |

OTHER PUBLICATIONS

Yetisen, A. K., Martinez-Hurtado, J. L., Ünal, B., Khademhosseini, A., & Butt, H. (2018). Wearables in medicine. Advanced Materials, 30(33), 1706910. (Year: 2018).*

(Continued)

*Primary Examiner* — Karlheinz R. Skowronek
*Assistant Examiner* — Mary C Leverett
(74) *Attorney, Agent, or Firm* — Caldwell Intellectual Property Law

(57) ABSTRACT

A system for determining a physical status of a subject, the system including a computing device configured to store a parameter classifier, the parameter classifier configured to classify biological extractions to physiological status parameters of subjects wherein the physiological status parameters include a nutrition parameter, an endurance parameter, and a strength parameter, receive biological extraction data of a subject, classify subject biological extraction to subject physiological parameters as a function of the stored parameter classifier, assign values to subject physiological status parameters as a function of the biological extraction data, indicate the physical status of the subject as a function of the subject physiological parameters, generate a physical guidance for the subject as a function of the physical status, and output the physical guidance.

14 Claims, 6 Drawing Sheets

(51) Int. Cl.
    *G16H 40/67*          (2018.01)
    *G16H 50/20*          (2018.01)
    *G16H 50/30*          (2018.01)

(56)                References Cited

U.S. PATENT DOCUMENTS

| | | | |
|---|---|---|---|
| 10,772,558 B2 | 9/2020 | Breuille et al. | |
| 2020/0121214 A1* | 4/2020 | Hyde | .......... A61B 7/04 |

OTHER PUBLICATIONS

Dias, Duarte, and João Paulo Silva Cunha. "Wearable health devices-vital sign monitoring, systems and technologies." Sensors 18.8 (2018): 2414. (Year: 2018).*

King, Rachel C., et al. "Application of data fusion techniques and technologies for wearable health monitoring." Medical engineering & physics 42 (2017): 1-12. (Year: 2017).*

Motti, Vivian Genaro, and Kelly Caine. "Micro interactions and multi dimensional graphical user interfaces in the design of wrist worn wearables." Proceedings of the human factors and ergonomics society annual meeting. vol. 59. No. 1. Sage CA: Los Angeles, CA: Sage Publications, 2015. (Year: 2015).*

* cited by examiner

METHODS AND SYSTEMS FOR DETERMINING THE PHYSICAL STATUS OF A SUBJECT

FIELD OF THE INVENTION

The present invention generally relates to the field of machine-learning. In particular, the present invention is directed to methods and systems for determining the physical status of a subject.

BACKGROUND

For decades, Westernized countries have observed a rise of the number of the elderly, the obese, and the infirm. It is often observed that those become frail and dependent on assistance. However, the development of frailty, obesity, and inability does not need to be inevitable. Appropriate guidance and training may prevent some negative developments. It is therefore desirable to assist in maintaining or achieving an acceptable physical status for a better quality of life.

SUMMARY OF THE DISCLOSURE

In an aspect, a system for determining a physical status of a subject, the system including a computing device configured to store a parameter classifier, the parameter classifier configured to classify biological extractions to physiological status parameters of subjects, wherein the physiological status parameters include a nutrition parameter, an endurance parameter, and a strength parameter, receive biological extraction data of a subject, classify subject biological extraction to subject physiological parameters as a function of the stored parameter classifier, assign values to subject physiological status parameters as a function of the biological extraction data, indicate the physical status of the subject as a function of the subject physiological parameters, generate a physical guidance for the subject as a function of the physical status, and output the physical guidance.

In another aspect, a method for determining a physical status of a subject, the method comprising storing, by a computing device, a parameter classifier, the parameter classifier configured to classify biological extractions to physiological status parameters of subjects, wherein the physiological status parameters include a nutrition parameter, an endurance parameter, and a strength parameter, receiving, by the computing device, biological extraction data of a subject, classifying, by the computing device, subject biological extraction to subject physiological parameters as a function of the stored parameter classifier, assigning, by the computing device, values to subject physiological status parameters as a function of the biological extraction data, indicating, by the computing device, the physical status of the subject as a function of the subject physiological parameters, generating, by the computing device, a physical guidance for the subject as a function of the physical status, and outputting, by the computing device, the physical guidance.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention.

However, it should be understood that the present invention is not limited to the precise arrangements and instrumentalities shown in the drawings, wherein.

The drawings are not necessarily to scale and may be illustrated by phantom lines, diagrammatic representations, and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for determining the physical status of a subject. In an embodiment, a computing device is configured for storing a parameter classifier configured to classify physiological status parameters to classes relating to nutrition and physical status of a subject. The parameter classifier may include a machine-learning model generated by a classification machine-learning process to categorize biological extraction training data to parameter classes, such as nutrition, endurance, and strength. The computing device is configured to assign values, such as numerical values, to the parameters of the subject as a function of the biological extraction data. Parameters may be classified, for instance by training a machine-learning model, into classes. Each class may then indicate the physical status of the subject. The computing device is configured to generate and output physical guidance as a function of the physical status of the subject.

Figure 1:
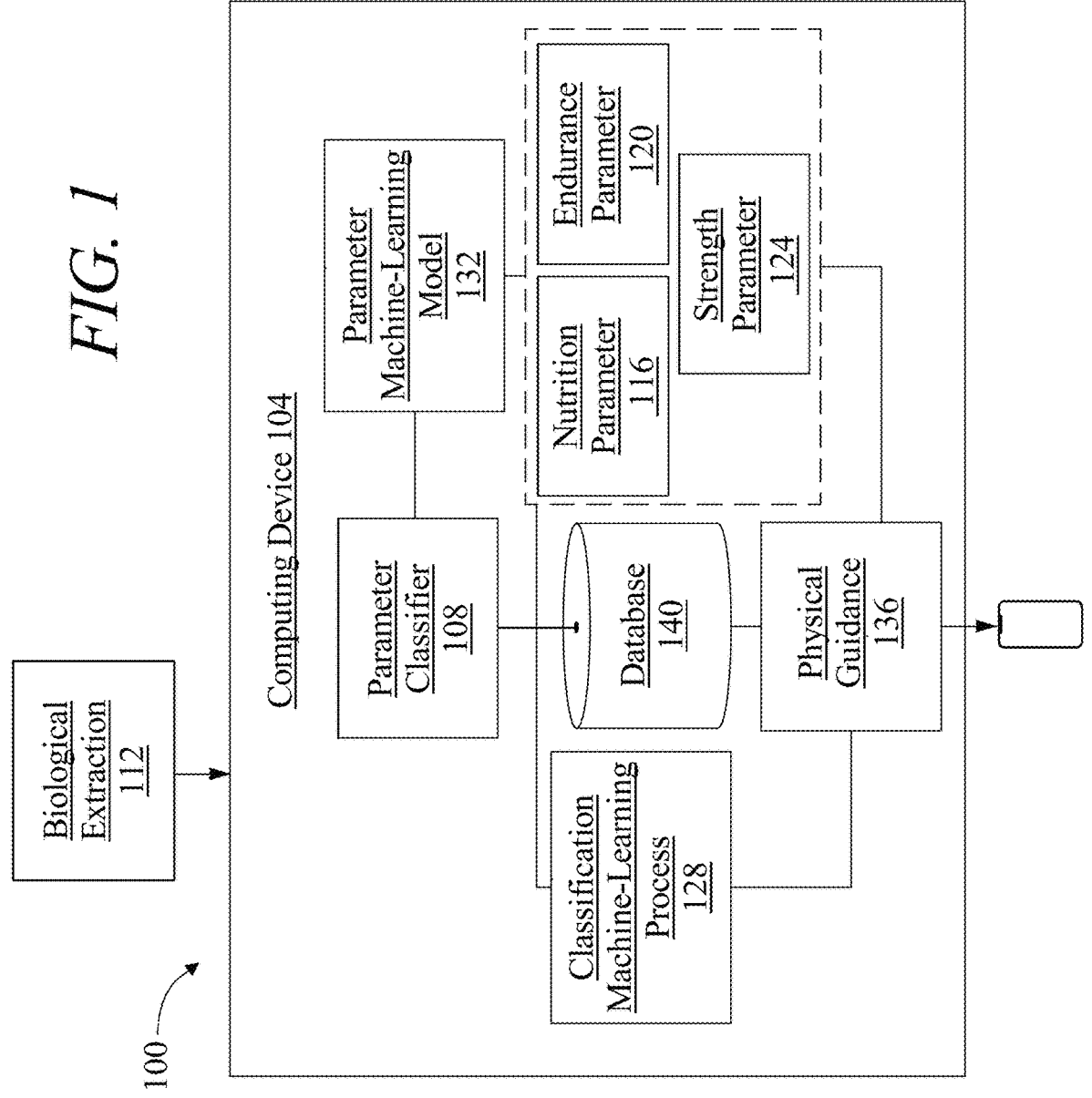
FIG. 1 is a block diagram illustrating a system for determining the physical status of a subject.

Referring now to FIG. 1, an exemplary embodiment of a system 100 for determining the physical status of a subject is illustrated. System includes a computing device 104. Computing device 104 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Computing device 104 may include a single computing device operating independently, or may include two or more computing device operating in concert, in parallel, sequentially or the like; two or more computing devices may be included together in a single computing device or in two or more computing devices. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Computing device 104 may include but is not limited to, for example, a computing device or cluster of computing devices in a first location and a second computing device or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device, which may operate in parallel, in series, redundantly, or in any other manner used for distribution of tasks or memory between computing devices. Computing device 104 may be implemented using a "shared nothing" architecture in which data is cached at the worker, in an embodiment, this may enable scalability of system 100 and/or computing device.

With continued reference to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Continuing in reference to FIG. 1, computing device configured to store a parameter classifier, the parameter classifier configured to classify physiological status parameters to classes relating to nutrition, endurance, and strength of subjects. A "parameter classifier," as used in this disclosure, is a classifier that is used for classifying biological extraction data to subject physiological status parameters, or to parameter classes, such as nutrition, endurance, and/or strength classes. A "classifier," as used in this disclosure, is a machine learning model that combines a discovery component (algorithm that matches a biological extraction datum to a parameter category) with a learning component (such as performing supervised learning, reinforcement learning, unsupervised learning, etc.), as described in further detail below. The classifier may include classifying biological extractions to physiological status parameters. A parameter classifier 108 may include a machine-learning model that is trained with training data containing a plurality of biological extraction data entries wherein each data entry is correlated to physiological status parameter categories, for instance and without limitation, classifying particular single nucleotide polymorphisms (SNPs) to nutrition parameter classes due to genetic difficulties in metabolism, nutrient adsorption, and micronutrient bioavailability, as described in further detail below. A "physiological status parameter," as used in this disclosure, is a classification of biological extraction data classified to a status category. Physiological status parameter may be simply referred to herein as, "physiological parameter." A physiological status parameter may include a variety of physiological status categories such as nutrition, endurance, strength, microbiome (flora), gut wall strength, intolerances, sleep, and the like. A physiological status parameter may include an endurance parameter, strength parameter, nutrition parameter, and/or a plurality of other parameters. At least a physiological status parameter may be summarized in a profile, summarized as a single numerical value, described as a function of values, or the like, that provides an overall "physical status," as described in further detail below.

Continuing in reference to FIG. 1, computing device 104 is configured to receive biological extraction data of a subject. A "biological extraction," as used in this disclosure, is chemical data, physiological data, medical data, and the like. Biological extraction 112 may include genetic data including the presence of single nucleotide polymorphisms (SNPs), mutations, allele designations (dominant, recessive, +/−, etc.), and the like; epigenetic data including methylation patterns, changes in gene expression patterns, enzyme concentrations and specific activity, and the like; microbiome data including gut microbiota, 'good' flora, transient flora, opportunistic pathogens, bacteria, viruses, parasites, fungi, circulating peptides, biologics, and the like; previous medical history including surgeries, treatments, prescriptions, current and past medications, allergies, family history of disease, diagnoses, prognoses, and the like; physiological data including systolic and diastolic blood pressure, resting heart rate, VO2 max, oxygen saturation, blood cell counts, hemoglobin/hematocrit levels, blood iron concentration, body mass index (BMI), blood sugar, HDL/LDL cholesterol levels, hormone levels, and the like; among any other data that one skilled in the art may recognize as biological extraction data that may be classified to a category, such as nutrition, endurance, and/or strength. Biological extraction 112 may include a variety of data, from a variety of sources, with the data originating from a single subject and/or a plurality of subjects, for instance and without limitation, as described in U.S. Nonprovisional application Ser. No. 16/886,647, filed on May 28, 2020, and entitled "METHODS AND SYSTEMS FOR DETERMINING A PLURALITY OF BIOLOGICAL OUTCOMES USING A PLURALITY OF DIMENSIONS OF BIOLOGICAL EXTRACTION USER DATA AND ARTIFICIAL INTELLIGENCE," the entirety of which is incorporated herein by reference.

Continuing in reference to FIG. 1, correlations that parameter classifier 108 may determine, describe, or otherwise model from, and/or that may be present in, training data may include correlations in an individual subject's biological extraction data. For instance and without limitation, single nucleotide polymorphisms SNPs found in metabolic genes (from genome sequencing) may relate to varying degrees of metabolic disease, distress, and/or difficulty; for instance SNPs in genes encoding enzymes found in the folate pathways in humans may relate to altered metabolism, which may affect the calculation of a nutrition parameter 116 with accompanying folate (vitamin B12) nutritional intake data, which may also effect endurance and strength to varying degrees. In further illustrative examples, blood chemistry data, such as from an extensive blood panel test provided to a subject may include data that relates to nutritional deficiencies (which may be correlated to dietary patterns, supplementation, and the like), ALT/AST/creatine kinase/creatine blood levels which may relate to a particular fitness level or endurance/strength in a subject, and the like. Correlations training data contains may include trends, patterns, and the like, correlated from biological extraction 112 data from a subcategory of subjects, such as 1,000 alike subjects, wherein parameter classifier 108 may determine "alike subjects" being alike based on certain biological extraction 112 identifiers, such as age, sex, and the like. For instance and without limitation, global variations in gene expression levels among alike populations of subjects may be useful to a correlating genomics, or an understanding of how genetic and epigenetic factors influence both normal variable traits and disease risk in humans. In non-limiting illustrative examples, global gene expression levels may be useful for determining a subject's endurance from blood panel data that correlating varying levels of exercise fitness to blood levels of ALT/AST/creatine kinase/creatine to physical endurance of a subject. In such an example, it may be found from blood panel data from 100's of marathon-runners that a certain threshold value of blood levels is associated with the endurance required to participate in a marathon. Additionally, correlations made between gene expression data in the training data may be useful to correlate to Diabetes, obesity, cancer, auto-immunological disorders, and the like, which may be useful to determining nutrition parameter 116 and/or useful in determining true nutrition targets for a subject. Correlations found in training data may relate a subject's propensity for anemia due to age, sex, exercise frequency, and nutritional input and correlated to subject serum iron levels (blood test data) to locate true nutrition targets for iron and determine a nutrition parameter 116 from the current iron nutritional input. Training data from a single subject, or plurality of subjects, may be recorded by a wearable device, physiological sensor such as a silver chloride garment trace, blood sugar monitor, bio-impedance monitor, physician assessment such as using an ECG/EEG monitor, a physical, and the like. Training data may originate from a plurality of subjects, physicians, laboratory technicians, genomic/proteomic studies, meta-data analyses, and the like, stored in a database, which may relate to a plurality of assessment tests, and the like.

Continuing in reference to FIG. 1, training data may originate from the subject, for instance via a questionnaire and a user interface with computing device 104, providing medical history data, retrieving whole genome sequencing, and the like. Training data may originate from an individual other than subject, including for instance an expert, physician, lab technician, nurse, caretaker, psychologist, therapist, and the like. Training data may be recorded and transmitted to computing device 104 via a wearable device such as a pedometer, gyrometer, accelerometer, motion tracking device, bioimpedance device, ECG/EKG/EEG data, physiological sensors, blood pressure monitor, blood sugar and VOC monitor, and the like. Training data may include data stored and/or retrieved from online research repositories, such as National Institutes of Health (NIH), clinical trials, peer-reviewed scientific research, laboratory results, and the like. Training data may originate from any number of subjects, wherein the training data may become more robust with increasing datasets from a greater number of subjects. Training data for any machine-learning process described herein may include data recorded by a physiological sensor and/or wearable device and received by computing device as biological extraction 112.

Continuing in reference to FIG. 1, biological extraction 112 may be classified to a nutrition parameter, for instance, by classifying biological extraction data that may relate to a subject's nutrition. As used in this disclosure, "nutrition" is a parameter category that includes data concerning a nutrient amount relating to a subject. A "nutrient amount," as used in this disclosure, is an amount of a nutrition for sustaining health, improving health, addressing a disease, addressing a symptom, prolonging longevity, improving athletic performance, or the like. A "nutrient parameter," as used in this disclose, is a qualitative and/or quantitative parameter that describes a subject's nutrition. A nutrient parameter 116 may include numerical values useful to determine nutrient amounts, including without limitation, nutrient surpluses, or an amount of nutrients a subject has consumed, metabolized, and/or absorbed in excess to what may be determined sufficient. A nutrient parameter 116 may include numerical values helpful in determining a nutrient deficiency, including without limitation, chronic and acute nutrient deficiencies wherein a subject has consumed, metabolized, and/or absorbed an amount of a nutrient that is below what may otherwise be necessary. A nutrient parameter 116 may include numerical values used for determining personalized, per-subject nutrient amounts for what is necessary to improve subject physiology, maintain athletic performance, improve lifestyle, address a disease, and the like.

Continuing in reference to FIG. 1, in non-limiting illustrative examples, a subject's biological extraction 112 may include data that may inform if a subject has a nutrient deficiency, such as low serum levels of iron, medical history of anemia, among other biological extraction 112, which may assist with determining a nutrition parameter 116. In further non-limiting illustrative examples, biological extraction 112 data relating to bone mineral density, history of osteoporosis, SNPs in calcitonin and other gene-related polypeptides, may be classified to a nutrition parameter 116 concerning a subject's mineral and vitamin profile including nutrient amounts for calcium, phosphorous, and/or vitamin D. In such an instance, the presence of a 'history of migraines' in a subject may include accompanying biological extraction 112 data including calcitonin gene-related peptide (CGRP) as a mediator of neurogenic inflammation, which may be classified to a nutrition category and be enumerated in the nutrition parameter 116. In such an example, a nutrition parameter 116 that originates from such biological extraction 112 may be useful for providing physical guidance for dietary recommendations that reduce inflammation in that subject, potentially addressing migraine frequency and intensity, and setting increased daily recommended amounts of these vitamins and minerals.

Continuing in reference to FIG. 1, biological extraction 112 may be classified to an endurance parameter, for instance, by classifying biological extraction 112 data that may relate to a subject's endurance. As used in this disclosure, "endurance," is a category to which biological extraction may be classified that describes a subject's ability to exert itself and remain active for a period of time, including the ability to resist, withstand, recover from, and have immunity to trauma, wounds, and/or fatigue. An "endurance parameter," as used in this disclosure, is a qualitative and/or quantitative parameter that describes a subject's endurance. Endurance parameter 120 may include a numerical value that describes physical endurance, for instance and without limitation, anaerobic endurance and/or cardiovascular endurance for physical stamina. Endurance parameter 120 may include a numerical value describing a subject's vitality and immunological homeostasis relating to immunity to pathogens, including the common cold viruses, respiratory infections, ear infections, and the like. Endurance parameter 120 may include a numerical value that describes a subject's and physical constitution, including skin plasticity and strength, tolerance of capsaicin, resistance and/or tolerance to poisons (such as alcohol), nootropics and/or stimulants (such as caffeine/nicotine), recreational drugs, and the like.

Continuing in reference to FIG. 1, in non-limiting illustrative examples, a subject's biological extraction 112 may include data that may inform how healthy and/or strong a subject's immune system is, or in other words the subject's immune endurance, such as serum immunoglobulin levels antibody activity, lymphocyte counts, stimulation assay results for measuring immune cell activation, among other biological extraction 112. For instance and without limitation, an endurance parameter 120 may be a score that relates to the number of times a subject has been sick such as falling ill 8 times a year, or 0.67 times per month. In such a case, that data may include biological extraction 112 that is classified to an endurance parameter 120 category that may be useful in determining an overall endurance parameter 120. In further non-limiting illustrative examples, a subject's 3-mile time, serum creatine levels, and the like, may be useful biological extraction for determining an endurance parameter 120 and may be classified to such a category, wherein the endurance parameter 120 may include a numerical value that incorporates the full spectrum of biological extraction 112 as it relates to the subject's overall endurance, for instance as a predictive value for how a subject may perform in a marathon.

Continuing in reference to FIG. 1, biological extraction 112 may be classified to a strength parameter, for instance, by classifying biological extraction data that may relate to a subject's strength. As used in this disclosure, "strength," is a category to which biological extraction may be classified that describes a subject's ability to exert force and/or pressure, including musculoskeletal performance. Strength may include musculoskeletal cross sectional area, such the hypertrophic quality of a quadricep. Strength may include a maximal force that subject may produce, such as measured by a hand-grip test, 1-rep-max weightlifting exercise, and the like. Strength may include relative tonnage, or mass by distance movement, by a subject relative to the subject's bodyweight, such as measured by a Sinclair coefficient. A "strength parameter," as used in this disclosure, is a qualitative and/or quantitative parameter that describes a subject's strength. Strength parameter 124 may include a numerical value that relates a subject's fitness routine to the subject's overall strength capability.

Continuing in reference to FIG. 1, the parameter classifier 108 configured to classify physiological status parameters may include generating the parameter classifier 108 using a classification machine-learning process to categorize biological extraction 112 data to physiological status parameter classes. Classification machine-learning process may include any machine-learning algorithm, program, model, and/or process as performed by a machine-learning module used by computing device 104, as described in further detail below. A "machine learning process," as used in this disclosure, is a process that automatedly uses a body of data known as "training data" and/or a "training set" to generate an algorithm that will be performed by a computing device/module to produce outputs given data provided as inputs; this is in contrast to a non-machine learning software program where the commands to be executed are determined in advance by a subject and written in a programming language. Training data for a classification machine-learning process 128 may be used for generating a machine-learning model (parameter classifier 108) using the training data. In non-limiting illustrative examples, training data may include blood protein and enzyme concentrations and specific activities for instance of fibrinogen, ferritin, serum amyloid A, α-1-acid glycoprotein, ceruloplasmin, hepcidin, haptoglobin, tumor necrosis factor-α (TNF-α), among other acute phase proteins; for instance cytokine identities and concentrations for instance interleukin-6 (IL-6); metabolites identities and concentrations such as blood sugar, LDL and HDL cholesterol content; hormone identities and concentrations such as insulin, androgens, cortisol, thyroid hormones, and the like; erythrocyte sedimentation rate, blood cell counts, plasma viscosity, and other biochemical, biophysical, and physiological properties regarding blood panels, blood tests, AST/ALT concentrations, and the like, for instance and without limitation as it relates to the three categories of physiological status parameters: nutrition, endurance, and/or strength. Training data may include data retrieved from online research repositories, such as National Institutes of Health (NIH), clinical trials, peer-reviewed scientific research, laboratory results, and the like. Parameter classifier 108 may be generated as a function of training data to 'learn' how to parse a subject's biological extraction (genetics, epigenetics, microbiome, blood panel, nutritional deficiencies, etc.) and classify to which physiological status parameter category. Classification machine-learning process 128 may be used to generate a classifier (machine-learning model) to 'know' how to categorize biological extraction elements to parameters; biological extraction 112 may originate from any number of subjects, wherein the classifier may become more robust with increasing training datasets.

Continuing in reference to FIG. 1, classification machine-learning process 128 may assign biological extraction 112 data to parameter categories by using training data to generate a machine-learning model, wherein the machine-learning model contains correlations, heuristics, and/or any mathematical relationships that may be determined from the training data. Machine-learning algorithm may include a supervised machine-learning algorithms, such as linear regression, k-nearest neighbors, naïve Bayes, neural networks, among other suitable supervised learning algorithms. Machine-learning algorithm may include unsupervised machine-learning algorithms, such as dimensionality reduction, clustering algorithms, among other suitable unsupervised learning algorithms. Parameters may include using a machine-learning algorithm to generate a graphical analysis describing, for instance and without limitation, the magnitude and/or effect each datum of biological has on each category.

Continuing in reference to FIG. 1, an endurance parameter 120 may be assigned by measuring the performance of an endurance test. An "endurance test," as used in this disclosure, is an assessment a subject may perform, or be the subject of, which generates data relating to the measure of endurance and/or stamina of the subject. For instance and without limitation, endurance test may assess the functional aerobic capacity which may be broadly described as a combination of cardiorespiratory fitness and functional ability. The former (cardiorespiratory fitness) refers to the ability of the circulatory and respiratory systems to provide oxygen to skeletal muscle and is characterized classically by the maximal oxygen consumption (VO2max), which may be measured directly during a maximal exercise test or indirectly by a submaximal test (heart rate measure). The latter (functional ability) generally refers to the ability of the individual to perform physical tasks (e.g. walk a given distance). Biological extraction 112 may include endurance test data. Parameter classifier 108 may classify biological extraction 112 containing endurance test data to endurance parameter class(es). The endurance assessment method may include at least one test for assessing the endurance of a subject (e.g. cardiorespiratory fitness) tested by high-intensity interval training (HIIT) and/or the functional ability of a subject (e.g. ability to perform given activity of daily living task such as walking). Tests may be classified further within the endurance classification, for instance by immunity, vitality, aerobic endurance, etc. The values obtained from at least one test for assessing the endurance of a subject may be scored and may be used to classify the endurance of the subject using a number of classes. A 'score' may include a numerical value, a vector, a function of values, a matrix of values, an array, or any other mathematical expression or method of representing a value or series of values associated with a class and/or test. Classes may be predetermined, such as using numerical value cutoffs. Classes may be determined by classifying endurance test assessment data to alike subjects, for instance and without limitation, 1,000 subjects who are of similar age, sex, lifestyle, BMI, disease, and symptom profile, etc. to generate a numerical value. Classes may be predetermined based on test, such as a bodyweight exercise class that is a category for pull-ups, chin-ups, pushups, sit ups, and other calisthenics exercises and fitness types, or a distance running class that contains data for distance-time of a subject.

Continuing in reference to FIG. 1, the determined classes for each endurance assessment may be combined (for multiple assessment methods) by assigning a numerical value to the classes, tests, and/or outcomes, and calculating an average value for each, combining the numerical values using a mathematical expression, and/or combining values in a weighted manner. The numerical value assigned to each test, or class that each test may belong to (such as immunity, vitality, aerobic capacity, bone density, muscle mass, integrity of joints, etc.) may be different for each class and may be incremental (e.g. on a whole number scale, by increases of '1'). Each class may indicate a certain endurance of a subject. For example and without limitation, a higher numerical value assigned to a class may indicate a higher endurance of said subject, wherein for every 10 seconds reduced on a subject's 3-mile run time is an increase of '1' in score, wherein decreasing the endurance test time for 3-mile run from 24 minutes to 23 minutes may increase the endurance parameter 120 and/or score by '10'. In a particular example, there may be three classes assigned to the values obtained in the endurance assessment tests and the classes may be designated as E1, E2, or E3, wherein E1 indicates that the measured endurance is below a certain lower predetermined limit, that may classify a subject in a particular category, and E3 indicates that the measured endurance is above a certain higher predetermined limit, that may classify a subject in a distinct category. E2 may indicate that the measured endurance is below a certain higher predetermined limit and is above a certain lower predetermined limit. This scheme of classes may also be defined to contain any number of classes with, or without, predetermined limits defining the membership to one class (e.g. E1, E2, E3, E4, E5). Limits may be determined by use of a classification machine-learning process to determine, provided a training data set of subjects, where numerical value limits for classes may lie according to performance on endurance tests.

Continuing in reference to FIG. 1, a strength parameter 124 may be assigned by measuring the performance of a strength test. A "strength test," as used in this disclosure, is an assessment a subject may perform, perform in, or be the subject of, which generates data relating to the measure of strength of the subject. Biological extraction 112 may include strength test data. Parameter classifier 108 may classify biological extraction 112 containing strength test data to strength parameter class(es). The strength assessment method may include at least one test for assessing the strength of a subject (e.g. 1 rep maximum (1RM) exertion) and/or the functional ability of a subject (e.g. handgrip strength, sit-to-stand test). Tests may be classified further within the strength classification, for instance by 1RM, grip strength, body part strength such as upper body strength, lower body strength, static strength, explosiveness, etc. The values obtained from at least one test for assessing the strength of a subject may be scored and may be used to classify the strength of the subject using a number of classes. A 'score' may include a numerical value, a vector, a function of values, a matrix of values, an array, or any other mathematical expression or method of representing a value or series of values associated with a class and/or test. Classes may be predetermined, such as using numerical value cutoffs. Classes may be determined by classifying strength test assessment data to alike subjects, for instance and without limitation, 1,000 subjects who are of similar age, sex, lifestyle, BMI, disease, and symptom profile, etc. to generate a numerical value. Classes may be predetermined based on test, such as a bodyweight exercise class that is a category for bench press, deadlift, squat, power clean, and other weightlifting exercises and/or fitness types of a subject.

Continuing in reference to FIG. 1, the determined classes for each strength assessment may be combined (for multiple assessment methods) by assigning a numerical value to the classes, tests, and/or outcomes, and calculating an average value for each, combining the numerical values using a mathematical expression, and/or combining values in a weighted manner. The numerical value assigned to each test, or class that each test may belong to (such as explosiveness, static holds, 1RM, etc.) may be different for each class and may be incremental (e.g. on a whole number scale, by increases of '1'). Each class may indicate a certain strength of a subject. For example and without limitation, a higher numerical value assigned to a class may indicate a higher strength of said subject, wherein for every 1 kilogram (kg), or 2.2 pounds (lbs.), increased on a subject's 1RM squat results in an increase of '1' in score, wherein increasing the strength as measured by 1RM squat by 20 kg may increase the strength parameter 124 and/or score by '20'. In a particular example, there may be three classes assigned to the values obtained in the strength assessment tests and the classes may be designated as S1, S2, or S3, wherein S1 indicates that the measured strength is below a certain lower predetermined limit, that may classify a subject in a particular category, and S3 indicates that the measured strength is above a certain higher predetermined limit, that may classify a subject in a distinct category. S2 may indicate that the measured strength is below a certain higher predetermined limit and is above a certain lower predetermined limit. This scheme of classes may also be defined to contain any number of classes with, or without, predetermined limits defining the membership to one class (e.g. S1, S2, S3, S4, S5). Limits may be determined by use of a classification machine-learning process to determine, provided a training data set of subjects, where numerical value limits for classes may lie according to performance on strength tests.

Continuing in reference to FIG. 1, a nutrition parameter 116 may be assigned by determining a nutritional input of the subject. Biological extraction 112 may include nutritional input data. A "nutritional input," as used in this disclosure, is nutritional intake of a subject as it relates to any of the categories or values represented by a nutritional need; nutritional intake may include subject-reported meals, food items, supplements, beverages, etc. that the subject has consumed. Parameter classifier 108 may classify biological extraction 112 containing nutritional input data to nutrition parameter class(es), such as chronic nutritional deficiencies (overs months), acute nutritional deficiencies (daily), nutritional surpluses, etc. Nutritional input values may be relative to the nutritional requirements of a subsect, for instance on a per-subject basis, wherein scores are normalized between subjects as relative to per-subject needs. For instance, a nominal score of '8' may be given to a subject that has consumed 80% of their per-subject daily intake of a particular nutrient, regardless of the mass amount of that nutrient and how it may differ subject-to-subject. In this way, if 100 nutrients (macronutrients, micronutrients, pro-recovery bioactive nutrients, targeted nutrients for addressing a disease, etc.) are tracked a nominal score of '1000' may represent achieving 100% of the recommended amounts of all nutrients, and a score of ~800 may represent achieving an average of ~80% of all nutrients. Nutritional input and per-subject nutritional needs may be determined for a subject, for instance, and without limitation, as described in U.S. Nonprovisional application Ser. No. 16/886,661, filed on May 28, 2020, and entitled "METHODS AND SYSTEMS FOR DETERMINING A PLURALITY OF NUTRITIONAL NEEDS TO GENERATE A NUTRIENT SUPPLEMENTATION PLAN USING ARTIFICIAL INTELLIGENCE," the entirety of which is incorporated herein by reference.

Continuing in reference to FIG. 1, a nutritional parameter 116 and/or nutrition class 'score' may include a numerical value, a vector, a function of values, a matrix of values, an array, or any other mathematical expression or method of representing a value or series of values associated with a class and/or test. Classes may be predetermined, such as using numerical value cutoffs. Classes may be determined by classifying nutritional input assessment data to alike subjects, for instance and without limitation, 1,000 subjects who are of similar age, sex, lifestyle, BMI, disease, and symptom profile, etc. to generate a numerical value. Classes may be predetermined based on nutritional input category, such as a nutritional deficiency class that is a category for macronutrient deficiency (diets too low in protein, too high in carbohydrates, diets lacking non-essential amino acids, essential amino acids, fats including non-essential fats, essential fats such as long-chain polyunsaturated fatty acids (LC-PUFAs), short-chain polyunsaturated fatty acids (SC-PUFAs), omega fatty acids, carbohydrates, including digestible and non-digestible carbohydrates such as dietary fiber, inulin, psyllium, and methylcellulose); micronutrient deficiency (such as vitamin A, thiamin (vitamin B1), riboflavin (vitamin B2), niacin (vitamin B3), pantothenic acid (vitamin B5), vitamin B6, biotin (vitamin B7), folate (vitamin B12), vitamin C, vitamin D2, vitamin D3, vitamin E, vitamin K1, vitamin K2; minerals such as calcium, phosphorous, potassium, sodium, magnesium; trace elements such as iron, sulfur, manganese, selenium, chromium, molybdenum, copper, cobalt); halides such a chloride and iodine; electrolytes and salts including bicarbonate, creatine, and phosphocreatine; caloric content, and the like, of a subject.

Continuing in reference to FIG. 1, each nutrition class may indicate a certain nutritional input of a subject. For example and without limitation, a higher numerical value assigned to a class may indicate a sufficient amount of a nutrient class in a subject, wherein for a subject with a daily recommended vitamin C during cold season being 200 milligrams (mg), for every 2 mg, a subject may receive an increase of '1' in score, wherein achieving 200 mg vitamin C may result in a nutrition parameter 116 and/or score of '100'. Computing device 104 may design an algorithm and/or equation for weighting a nutritional surplus of vitamin C to not ablate a lower score in a second nutritional deficiency class. In a particular example, there may be three classes assigned to the values obtained in the nutritional input assessment and the classes may be designated as N1, N2, or N3, wherein N1 indicates that the measured nutritional input is below a certain lower predetermined limit, that may classify a subject in a particular category, and N3 indicates that the measured nutritional input is above a certain higher predetermined limit, that may classify a subject in a distinct category. N2 may indicate that the measured nutritional input is below a certain higher predetermined limit and is above a certain lower predetermined limit. This scheme of classes may also be defined to contain any number of classes with, or without, predetermined limits defining the membership to one class (e.g. N1, N2, N3, N4, N5). Limits may be determined by use of a classification machine-learning process to determine, provided a training data set of subjects, where numerical value limits for classes may lie according to performance on strength tests.

Continuing in reference to FIG. 1, the system 100 may determine the suitability of the subject for system 100 and/or a test used therein as described in this disclosure. For instance, prior to providing a test computing device 104 may determine whether the subject is suitable for being subject to the test. Computing device 104 is configured to receive biological extraction 112 of a subject and may classify the data, for instance by age, fitness level, disease state, genetic profile, etc., to determine suitable assessment tests for endurance, strength, and/or nutritional input. As used in this disclosure, "suitable," or "suitability" of a subject for a test and/or for system 100 is a determination of the appropriateness of a particular assessment test and/or system for the subject. Determining whether system 100 is "suitable" for a subject may include parsing biological extraction 112 data using computing device 104 to locate data for a questionnaire or other assessment of readiness for a test, or applicability of a test for assessing the subject. For instance and without limitation, the Physical Activity Readiness Questionnaire (PAR-Q) serves to quickly check that the tests and exercises that are proposed are medically safe from a cardiac point of view. Depending on the PAR-Q result, subject will do a walk test (e.g. a 4 m walk test) to do a first evaluation of their physical capacity: they will have to do a walk over a certain distance where the subject is asked to walk over said distance with the maximum possible speed. The measured speed of the subject over said distance allows to determine whether the subject qualifies for the main assessment method. A measured value that is below a predetermined lower limit may indicate that the subject is not suitable for the main assessment. In such a case, the subject may be too frail, disabled, or otherwise not suited to the assessment, and the subject should undergo further medical examination, for example, performed by a geriatrician. A measured value that is above a predetermined upper limit may indicate that the subject is not suitable for the main assessment either. In those cases, the subject is usually sufficiently healthy and according to lifestyle, or other biological extraction 112 data, may require a more intense or challenging assessment test to accurately describe the subject's endurance, strength, and the like. In non-limiting illustrated examples, computing device 104 may set a measured value that is between a predetermined lower limit and a predetermined upper limit indicates that the subject is suitable for the main assessment. Such predetermined limits may be found, for instance using a web browser and the Internet, for the PAR-Q test.

Continuing in reference to FIG. 1, for instance and without limitation, older adults (above 65 years of age) with relatively little fitness background and evidence of frailty, an endurance assessment test may include walk speed test, strength assessment test may include grip strength and sit-to-stand tests, and nutrition assessment may include mini nutritional assessment (MNA) test to evaluate protein intake. Computing device 104 may classify such an elderly subject to these assessment tests based on data received as part of biological extraction 112 (age, fitness level as evidenced by various biomarkers, nutritional input including protein mass intake, etc.). Computing device 104 may determine "suitability" of subject for being "subject to the system 100" by using a classification machine-learning process, as described above, for instance as used to generate parameter classifier 108. Computing device 104 may determine parameters for a subject having received biological extraction 112, even if subject may not be suitable for a particular assessment test. The degree to which an assessment test is "suitable" for a subject may be described by a numerical value, function, mathematical expression, percentile, or the like, that is a quantitative and/or qualitative measure of the matching of an assessment test for a subject depending upon the classification of the subject to a class— i.e. a 65 year old man lacking fitness experience versus a 25 year old woman who trains for marathons may be classified in different categories, each represented with a different identifier, which assigns different endurance, strength, and nutritional assessment tests. The suitability of an assessment test may be calculated as a numerical value, such as a percentile, that computing device 104 uses to match a subject to a test, for example 'subject is $60^{th}$ percentile for a 3-mile run endurance test', wherein the percentile may represent the likelihood the subject may complete the test and/or the probability the test may provide reliable test data for determining an accurate physiological status parameter score.

Continuing in reference to FIG. 1, computing device 104 may determine threshold values for assigning assessment tests based on biological extraction classification. For instance, computing device 104 may assign an assessment test as a function of a threshold value for the test wherein a score within a certain numerical value range for a subject assigns a test—i.e. score from 0-10 is a walk speed endurance test, 11-20 is 1-mile run endurance test, 21-30 is 2-mile, 31-40 is 3-mile, 50+ is 5-mile, etc. In such a case, the cutoff threshold value may relate to the parameter score, for instance an endurance parameter 120 of '35' may relate to the assignment of a 3-mile test for further assessment of the endurance. This may improve the accuracy of a parameter value by assigning a test with a predicted or expected performance by the subject as evidenced by the parameter and may 'teach' computing device 104 how to assign values to the parameters to increase and/or decrease a value and by what magnitude.

Continuing in reference to FIG. 1, computing device 104 is configured to assign values to the parameters of the subject as a function of the biological extraction 112 data. Assigning values to the parameters may include training a parameter machine-learning model with training data that includes a plurality of data entries wherein each data entry is correlated to a numerical scale for each parameter and assigning the values as a function of the parameter machine-learning model. A parameter machine-learning model may include any machine-learning algorithm, process, and/or method described herein as performed by a machine-learning module, as described in further detail below. Parameter machine-learning model 132 may derive numerical scales that determine, for instance, number lines along which parameters may be provided values. Parameter machine-learning model 132 may derive such numerical scales by training with training data, as described above, and in further detail below. Training data may include, for instance and without limitation, a set of repetitions of maximal force (1RM) and acceleration vectors associated with the movements used for weight training exercises for subjects of a range of ages, weight, sex, and BMI indexes, wherein the performance of subjects may be plotted among an (x, y) plot giving rise to, for instance a Gaussian distribution (normal distribution) along which the trends and/or mathematical relationships between age, fitness level, BMI, sex, etc. may relate to the average performance of subjects for assigning a scoring scale. In such an example, a numerical scale may be assigned to a strength parameter 124 determined by a series of 1RM tests given to subjects according to their biological extraction 108. A series of numerical scales may be determined by parameter machine-learning model 132 using training data directed to each class of a parameter; for instance and without limitation, there may exist 100's of categories for nutritional parameter 116 wherein each macronutrient, micronutrient, and sub-type of each and/or combination thereof is assigned to an individual class and provided an individual scoring criteria (numerical scale). Each numerical scale may be determined using training data from a single subject, or a plurality of subjects. Persons skilled in the art may appreciate that increasing the training data set data points, and more concise classification of subjects (such as to tighter age windows, etc.) may increase the robustness of assigning numerical values to parameters.

Continuing in reference to FIG. 1, in non-limiting illustrative examples, a nutrition parameter 116 may include 100's of classes, or sub-designations directed to each individual nutrient that is being measured in the nutrition parameter 116, each of which is assigned a value according to an individual numerical scale. The numerical scales me be on the same range of values, for instance all on a 0-100 scale; alternatively or additionally they may receive different numerical scales. The plurality of individual numerical values assigned to each class within the 'nutrition parameter' classification may be combined into a singular numerical value for the nutrition parameter 116. In non-limiting illustrative examples, numerical values for individual classes may be combined using a mathematical expression such as a summation series wherein each element is weighted individually using a multiplicative (scalar) value. Alternatively or additionally, despite a nutrition parameter 116 providing a subject a singular numerical value, system 100 may also provide subject an umbrella of tabular individual numerical values relating to each individual nutrient category and its impact on the overall nutrition parameter 116.

Continuing in reference to FIG. 1, assigning values to subject physiological status parameters of the system may be repeated in defined intervals. As used in this disclosure, "defined interval," is a period of time that computing device 104 may use to update biological extraction 112, calculate parameters, or any other determination by system. Defined intervals may include repeating the steps in defined intervals, for instance every 8-16 weeks, wherein 'steps' may include assigning assessment tests, assigning values to parameters, retrieving and/or updating biological extraction 112, generating training data, generating and/or updating classifiers defined herein, etc. Defined intervals may include monthly assignment of tests and/or recalculation of parameters based on biological extraction 112. Defined intervals may include weekly parameter updates. Defined interval may include different time windows for different parameters, for instance updating nutritional parameter 116 daily, endurance parameter 120 monthly, and strength parameter 124 every '2 months'. Defined intervals may include real-time updates, for instance as soon as a subject-reported meal is received by computing device 104 as a nutritional input, as described above, computing device 104 may repeat steps of system 100 to generate a new nutrition parameter 116. Defined intervals may include real-time updates for instance as determined from a wearable device collecting fitness data, a 'macro' tracking application, etc.

Continuing in reference to FIG. 1, defined intervals may be set by computing device 104 using reactive computing. "Reactive computing," as used in this disclosure is a declarative programming paradigm that is concerned with data streams and the propagation of change in such data over sampled time period. Reactive computing may also be referred to as "reactive programming." Reactive computing may be used to iterative sample data inputs and, according to an internal "clock", generate iterative outputs (assessment test, numerical scales, classifying subject data, nutrition parameters 116, endurance parameters 120, strength parameters 124, etc.) in real-time, as the input data is collected. As used in this disclosure, input data may be a plurality of biological extraction data, for instance as detected by at least a sensor, such as a wearable fitness tracker, subject-reported meal, calorie tracking application, telemedicine application, etc., and received by computing device 104. Input data may include data that is generated as training data Computing device 104 may be configured, using reactive computing, to express static (such as arrays) and/or dynamic (such as event emitters) "data streams" with relative ease, and also communicate an inferred dependence within the associated "execution model" which facilitate the automatic propagation of the changed data flow. For instance, computing device 104 may be configured to employ a trained machine-learning model, which describes a mathematical relationship between a particular input to a particular subject datum as the "execution model" to automatically propagate outputs form the incoming signal data. Essentially, computing device 104 may use reactive computing to iterative receive biological extraction 112 (inputs) and refine parameter numerical values (outputs) at regular scheduled intervals, including when data is received (real-time), according to trained machine-learning models such as the classification machine-learning model, parameter machine-learning model 132, and the like. Computing device 104 may use the parameter classifier 108 (trained machine-learning model) to classify incoming biological extraction 112 data as it is received, wherein the trained parameter machine-learning model 132 may 'know' the impact to a parameter to which the biological extraction 112 belongs, and iteratively update the parameter according to the numerical scale that assigns a numerical value to the parameter-classified biological extraction 112.

Continuing in reference to FIG. 1, reactive computing may be simply expressed as a:=b+c wherein a is automatically updated whenever the values of b or c change, without the program having to re-execute the statement a:=b+c to determine the presently assigned value of a. Reactive computing used herein may be "model-view-controller" (MVC) architecture, wherein reactive programming may facilitate changes in an underlying model that are reflected automatically in an associated view. For instance, a trained parameter machine-learning model 132, which may correlate classified biological extraction 112 to numerical scales, wherein numerical scale may be used to assign to numerical values to the parameter. Reactive computing may be performed by computing device 104 using reactive extensions, such as RxJs, RxJAva, RxPy, RxSwift, and other APIs. Reactive computing may be implemented using any type of change propagation algorithm, such as a pull, push, and/or push-pull type approach to data propagation. Reactive computing may be any object-oriented reactive programming (OORP), functional reactive programming (FRP), or the like. Reactive programming may be implemented using for instance rule-based reactive programming languages such as through using relation algebra with Ampersand, Elm, and/or Observable. Persons skilled in the art, upon review of this disclosure in its entirety, will be aware of the various ways in which to implement reactive computing to sample biological extraction 112 during subject activity and provide parameter updates in real-time, or at any defined interval.

Continuing in reference to FIG. 1, classify the subject into classes as a function of each of the parameters. Computing device 104 may assign the subject into a class according to the numerical value assigned to each parameter from biological extraction, as described above. The numerical values assigned to each parameter for a subject may be used to place that subject into a class. Computing device 104 may classify subjects into classes using, for instance, numerical value cutoffs wherein a parameter above, below, or within a range of a value may place the subject into a particular class. Computing device 104 may classify the subject into a class using a mathematical expression that combines the parameters, such as using addition to combine parameter values. Computing device 104 may classify subjects as a function of a machine-learning process, such as a classification machine-learning process, as described above, for parameter classifier 108 which classifies subject according to alike subject parameter groupings. Classes may designate the physical status of the subject, for instance and without limitation for strength parameter 124 classes of 'novice', 'beginner', 'intermediate', 'advanced', 'elite', and 'world class' designations of strength, wherein a 'novice' class individual may have no fitness or strength background and poor posture, but an 'advanced' class may include subjects with considerable training experience and strength. According to a subject's classification, as a function of their nutrition parameter 116, endurance parameter 120, strength parameter 124, and/or combinations thereof, computing device 104 may 'learn' how to provide guidance to the subject.

Continuing in reference to FIG. 1, computing device 104 is configured to generate physical guidance for the subject as a function of the physical status. As used in this disclosure, "physical guidance," is a recommendation, suggestion, regimen, program, and/or guidance, intended for a subject according to the physical status of the subject. The "physical status," as used in this disclosure, is a physical status of the subject derived from biological extraction 112. A "physical status," may include a profile of the subject that includes at least a physiological status parameter, such as a nutrition parameter 116, endurance parameter 120, and/or strength parameter 124. Physical guidance 136 may include guidance intended to improve the subject's health, physiology, and the like, as evidenced by the parameters derived from the subject's biological extraction 112 and according to the physical status of the subject. A physical guidance 136 may include a customized fitness regimen according to a subject's physiological status parameters (physical status), for instance and without limitation, as described in U.S. Nonprovisional application Ser. No. 17/032,066, filed on Sep. 25, 2020, and entitled "METHODS AND SYSTEMS FOR GENERATING PHYSICAL ACTIVITY SETS FOR A HUMAN SUBJECT," the entirety of which is incorporated herein by reference. A physical guidance 136 may include customized, per-subject nutritional plans aimed at increasing nutrition parameter 116, for instance and without limitation, as described in U.S. Nonprovisional application Ser. No. 16/837,233, filed on Apr. 1, 2020, and entitled "METHODS AND SYSTEMS FOR GENERATING AN ALIMENTARY INSTRUCTION SET IDENTIFYING AN INDIVIDUAL PROGNOSTIC MITIGATION PLAN," the entirety of which is incorporated herein by reference. A physical guidance 136 may include instructions for a particular wearable device to assist with improving parameters, for instance and without limitation, as described in U.S. Nonprovisional application Ser. No. 17/062,710, filed on Oct. 5, 2020, and entitled "SYSTEM AND METHOD FOR PRESENTING A MONITORING DEVICE IDENTIFICATION," the entirety of which is incorporated herein by reference. Physical guidance 136 may be different for each determined class but also according to individual preferences.

Continuing in reference to FIG. 1, computing device 104 is configured to output the physical guidance 136. Output may be based on the results of the main assessment (parameters and classification), each subject may be provided a physical guidance 136 to be enrolled in, including for instance, a personalized nutrition and exercise program. Such a program may last for any amount of time, for instance 8 to 26, 12-20, or about 16 weeks. Progress and compliance with a program may be optionally controlled by monitoring habitual activity, for instance via subject-reported input via a graphical user interface, receiving biological extraction via a wearable device, and the like. After this personalized nutrition and exercise program is completed, additional assessment may be recommended as a physical guidance 136, for instance a strength assessment, endurance assessment, and nutrition assessment. In this way, progress of the subject with regard to the measured parameters may be determined. Based on the report of the progress the personalized nutrition and exercise program may be modified or cancelled. Thus, the method of the invention allows to periodically modify the personalized physical guidance 136 based on the results of the assessment and the classification of the subject according to their biological extraction to optimize the benefit for the subject. Accordingly, in an embodiment the invention relates to an iterative process wherein based on the results of the main assessment a personalized nutrition and exercise program may be chosen and the effects of said program are reassessed after a defined period, and based on such a reassessment, the physical guidance 136 is modified. These steps may be performed indefinitely. Prior to this feedback loop the method may include a pre-assessment to decide whether a person is suitable for being subject to the assessment.

Continuing in reference to FIG. 1, providing the physical guidance 136 may include generating a representation, via a graphical user interface, of the physical guidance. A "graphical user interface," as used in this disclosure, is any form of a user interface that allows a subject to interface with an electronic device through graphical icons, audio indicators, text-based interface, typed command labels, text navigation, and the like, wherein the interface is configured to provide information to the user and accept input from the user. Graphical user interface may accept user input, wherein user input may include an interaction with a user device. A user device may include computing device 104, a "smartphone," cellular mobile phone, desktop computer, laptop, tablet computer, internet-of-things (IOT) device, wearable device, among other devices. User device may include any device that is capable for communicating with computing device 104. User device and/or graphical user interface may store and/or retrieve I/O, such as parameters, from a database 140. Database 140 may include any data structure suitable for system 100, as described in further detail below. User device may receive physical guidance 136, for instance via a data network technology such as 3G, 4G/LTE, Wi-Fi (IEEE 802.11 family standards), and the like. User device may include devices that communicate using other mobile communication technologies, or any combination thereof, for short-range wireless communication (for instance, using Bluetooth and/or Bluetooth LE standards, AirDrop, Wi-Fi, NFC, etc.), and the like.

Continuing in reference to FIG. 1, generating a representation of physical guidance 136 may include displaying instruction sets, parameter values, and the like, via the graphical user interface. Subject may provide input, via an interaction with a user device, to select recommendations, indicate willingness to participate, not participate, and/or want alternatives to physical guidance 136. Generating a representation of physical guidance 136 may include hyperlinked elements, which guide the subject to a document, blog, website, online ordering site, or the like. Generating a representation of physical guidance 136 may include directing the subject to a "compatible element," such as one or more products, ingredients, merchandise, additive, component compound, mixture, constituent, element, article, and/or information content that is compatible with a subject, for instance and without limitation, as described in U.S. Nonprovisional application Ser. No. 17/087,727, filed on Nov. 3, 2020, and entitled "METHODS AND SYSTEMS FOR USING ARTIFICIAL INTELLIGENCE TO ANALYZE USER ACTIVITY DATA," the entirety of which is incorporated herein by reference.

Continuing in reference to FIG. 1, providing physical guidance 136 may include providing, to the subject, at least a wearable device identity associated with measuring the physical guidance 136. A "wearable device," as used in this disclosure, is any device which may gather biological extraction data from a subject, directly or indirectly, and communicate such data to computing device 104. Wearable device may be in contact with subject, in contact with subject's skin, and/or within proximity of subject. Wearable device may include a pedometer, accelerometer, gyroscope, bioimpedance monitor, glucose monitor, VOC monitor, heart rate monitor, blood pressure monitor, video capture, audio capture, etc. Wearable device may record data from assessment test. Wearable device may record biological extraction data 112. Physical guidance 136 may include an identity of a wearable, such as a 'pedometer' to assist with measuring the data from an assessment test, such as a walking endurance assessment, as described above. Wearable device may measure physical guidance 136 in that it may measure phenomenon directly resulting from, for instance, nutritional intake (blood sugar monitoring, etc.), endurance workouts (pedometer, etc.), and/or strength training (fitness tracking device, accelerometer, etc.). Wearable device may measure adherence and participation in physical guidance 136. Wearable device may ease the burden on subject in providing biological extraction 112 to system for calculation and/or recalculation of parameter.

Figure 2:
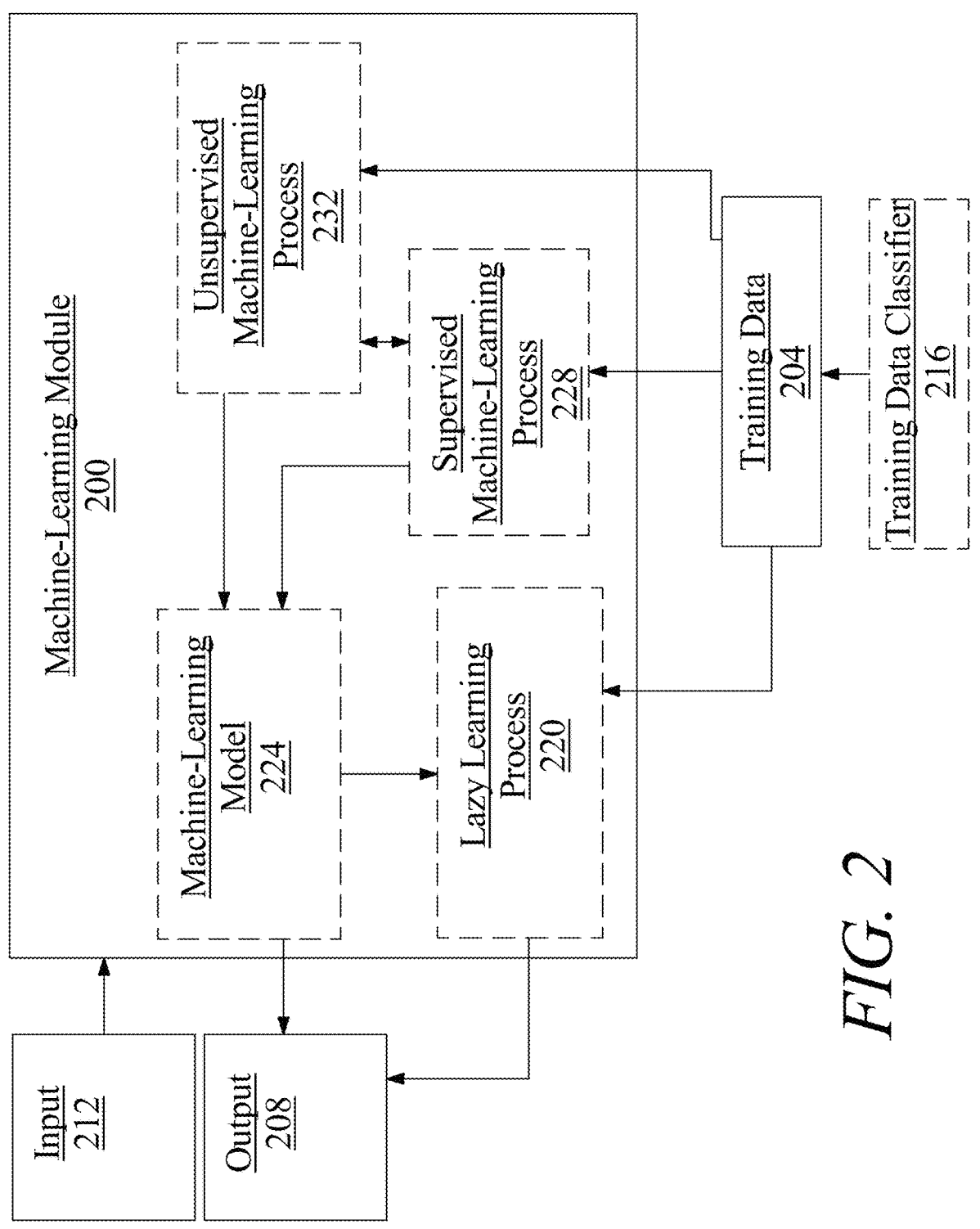
FIG. 2 is a block diagram of a non-limiting exemplary embodiment of a machine-learning module.

Referring now to FIG. 2, an exemplary embodiment of a machine-learning module 200 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 204 to generate an algorithm that will be performed by a computing device/module to produce outputs 208 given data provided as inputs 212; this is in contrast to a non-machine learning software program where the commands to be executed are determined in advance by a subject and written in a programming language.

Still referring to FIG. 2, "training data," as used herein, is data containing correlations that a machine-learning process may use to model relationships between two or more categories of data elements. For instance, and without limitation, training data 204 may include a plurality of data entries, each entry representing a set of data elements that were recorded, received, and/or generated together; data elements may be correlated by shared existence in a given data entry, by proximity in a given data entry, or the like. Multiple data entries in training data 204 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 204 according to various correlations; correlations may indicate causative and/or predictive links between categories of data elements, which may be modeled as relationships such as mathematical relationships by machine-learning processes as described in further detail below. Training data 204 may be formatted and/or organized by categories of data elements, for instance by associating data elements with one or more descriptors corresponding to categories of data elements. As a non-limiting example, training data 204 may include data entered in standardized forms by persons or processes, such that entry of a given data element in a given field in a form may be mapped to one or more descriptors of categories. Elements in training data 204 may be linked to descriptors of categories by tags, tokens, or other data elements; for instance, and without limitation, training data 204 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 2, training data 204 may include one or more elements that are not categorized; that is, training data 204 may not be formatted or contain descriptors for some elements of data. Machine-learning algorithms and/or other processes may sort training data 204 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 204 to be made applicable for two or more distinct machine-learning algorithms as described in further detail herein. Training data 204 used by machine-learning module 200 may correlate any input data as described in this disclosure to any output data as described in this disclosure.

Further referring to FIG. 2, training data may be filtered, sorted, and/or selected using one or more supervised and/or unsupervised machine-learning processes and/or models as described in further detail herein; such models may include without limitation a training data classifier 216. Training data classifier 216 may include a "classifier," which as used in this disclosure is a machine-learning model as defined herein, such as a mathematical model, neural net, or program generated by a machine learning algorithm known as a "classification algorithm," as described in further detail herein, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 200 may generate a classifier using a classification algorithm, defined as a process whereby a computing device and/or any module and/or component operating thereon derives a classifier from training data 204. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 216 may classify elements of training data to elements that characterizes a sub-population, such as a subset of biological extraction (such as gene expression patterns as it relates to common nutritional deficiencies) as a function of parameters or a subset of physical guidance 136 for a particular parameter class, numerical value, and/or other analyzed items and/or phenomena for which a subset of training data may be selected.

Still referring to FIG. 2, machine-learning module 200 may be configured to perform a lazy-learning process 220 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of predictions may be performed to cover an initial heuristic and/or "first guess" at an output and/or relationship. As a non-limiting example, an initial heuristic may include a ranking of associations between inputs and elements of training data 204. Heuristic may include selecting some number of highest-ranking associations and/or training data 204 elements, such as classifying biological extraction elements to a parameter category and assigning a value to the parameter as a function of some ranking association between elements (biological extraction 112 to parameter value). Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail herein.

Alternatively or additionally, and with continued reference to FIG. 2, machine-learning processes as described in this disclosure may be used to generate machine-learning models 224. A "machine-learning model," as used in this disclosure, is a mathematical and/or algorithmic representation of a relationship between inputs and outputs, as generated using any machine-learning process including without limitation any process as described above, and stored in memory; an input is submitted to a machine-learning model 224 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 224 may be generated by creating an artificial neural network, such as a convolutional neural network comprising an input layer of nodes, one or more intermediate layers, and an output layer of nodes. Connections between nodes may be created via the process of "training" the network, in which elements from a training data 204 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. A machine-learning model may be used as to derive numerical scales for providing numerical values to parameters, as described above, to "learn" the upper and lower limits to the scale, the increments to providing scoring, and the criteria for increasing and decreasing the parameter value. A machine-learning model may be used to "learn" which elements of biological extraction 112 belong to which parameter, and which values of parameters relate to which physical guidance 136.

Still referring to FIG. 2, machine-learning algorithms may include at least a supervised machine-learning process 228. At least a supervised machine-learning process 228, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include a plurality of parameters (potentially classified into categories), as described above as inputs, physical guidance 136 as outputs as it related to classified parameters, and a ranking function representing a desired form of relationship to be detected between inputs and outputs; ranking function may, for instance, seek to maximize the probability that a given input and/or combination of elements inputs is associated with a given output to minimize the probability that a given input is not associated with a given output, for instance in finding the most suitable physical guidance 136. Ranking function may be expressed as a risk function representing an "expected loss" of an algorithm relating inputs to outputs, where loss is computed as an error function representing a degree to which a prediction generated by the relation is incorrect when compared to a given input-output pair provided in training data 204. Persons skilled in the art, upon reviewing the entirety of this disclosure, will be aware of various possible variations of at least a supervised machine-learning process 228 that may be used to determine relation between inputs and outputs. Supervised machine-learning processes may include classification algorithms as defined above.

Further referring to FIG. 2, machine learning processes may include at least an unsupervised machine-learning processes 232. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 2, machine-learning module 200 may be designed and configured to create a machine-learning model 224 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 2, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Still referring to FIG. 2, models may be generated using alternative or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training data 204 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using training data 204.

Figure 3:
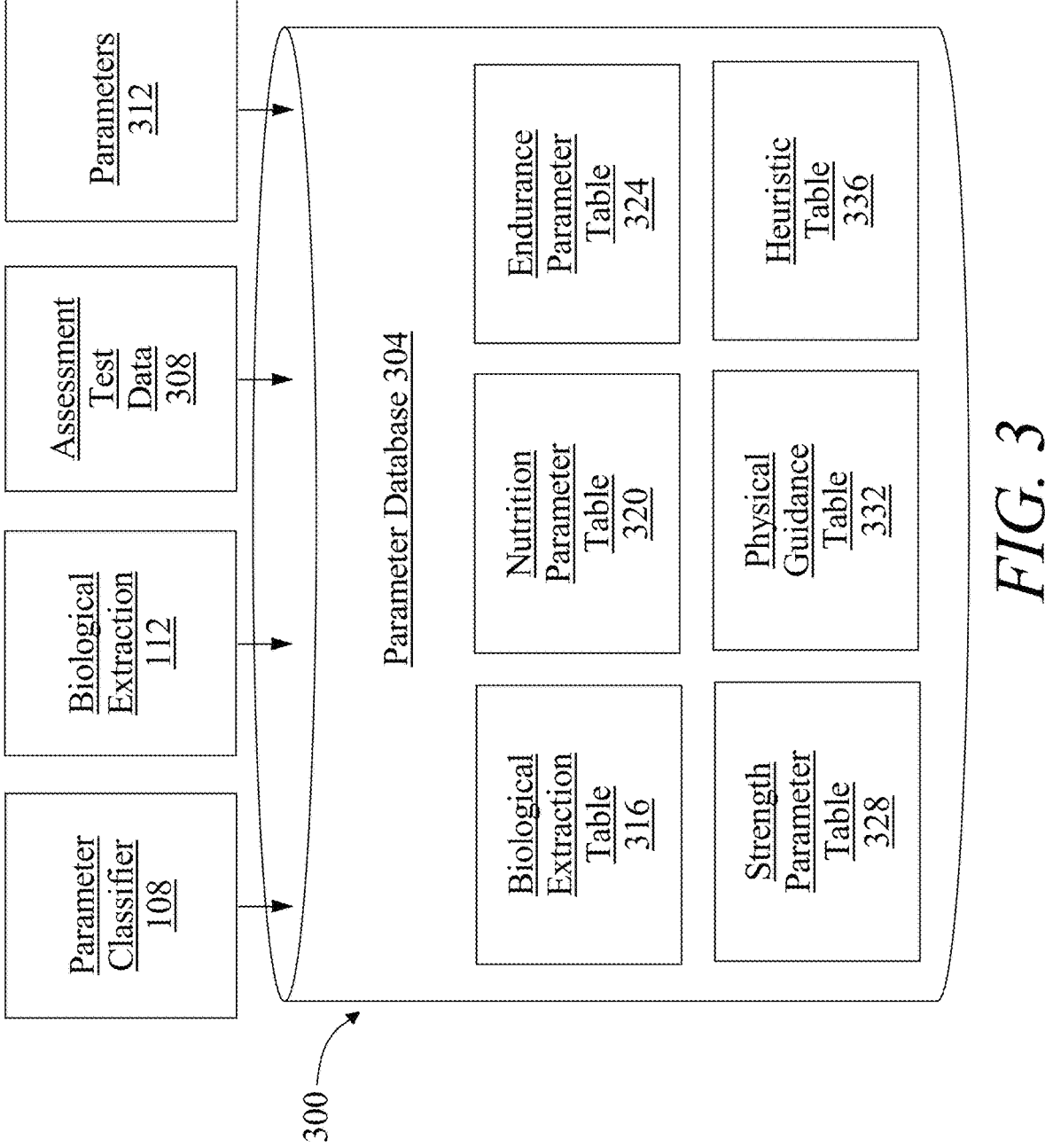
FIG. 3 is a block diagram of a non-limiting exemplary embodiment of a physical status database.

Referring now to FIG. 3, an exemplary embodiment 300 of a parameter database 304 is illustrated. Parameters for a plurality of subjects, for instance for generating a parameter classifier 108, may be stored and/or retrieved in parameter database 304. Biological extraction 112 data from a plurality of subjects for generating training data may also be stored and/or retrieved from a parameter database 304. Computing device 104 may receive, store, and/or retrieve training data, wearable device data, and the like, from parameter database 304. Computing device 104 may record, receive, and/or store assessment test data 308, for instance from an endurance or strength assessment test. Computing device 104 may organize assessment test data 308 for generating training data to train a machine-learning model. Computing device 104 may record, receive, and/or store parameters 312, for instance and without limitation, include nutrition parameter 116, endurance parameter 120, strength parameter 124, and/or a variety of other parameters.

Continuing in reference to FIG. 3, computing device 104 may store and/or parameter classifier 108, biological extraction 112, parameters, physical guidance 136, classifiers, among other determinations, I/O data, models, and the like, in a parameter database 304. Parameter database 304 may be implemented, without limitation, as a relational database, a key-value retrieval database such as a NOSQL database, or any other format or structure for use as a database that a person skilled in the art would recognize as suitable upon review of the entirety of this disclosure. Parameter database 304 may alternatively or additionally be implemented using a distributed data storage protocol and/or data structure, such as a distributed hash table and the like. Parameter database 304 may include a plurality of data entries and/or records, as described above. Data entries in a parameter database 304 may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a database may store, retrieve, organize, and/or reflect data and/or records as used herein, as well as categories and/or populations of data consistent with this disclosure. Computing device 104 may retrieve any determinations, as described herein, from the parameter database 304, such as nutrition parameters 116, endurance parameters 120, strength parameters 124, threshold values, numerical scales, physical guidance 136, and the like.

Further referring to FIG. 3, parameter database 304 may include, without limitation, biological extraction table 316, nutrition parameter table 320, endurance parameter table 324, strength parameter table 328, physical guidance table 332, and/or heuristic table 336. Determinations by a machine-learning process, machine-learning model, ranking function, and/or classifier, may also be stored and/or retrieved from the parameter database 304, for instance in non-limiting examples, physical guidance 136 according to a particular parameter classification, biological extraction 112 classified to parameter categories, biological extraction 112 cutoff values (such as gene expression levels to parameter values), and the like. As a non-limiting example, parameter database 304 may organize data according to one or more instruction tables. One or more parameter database 304 tables may be linked to one another by, for instance in a non-limiting example, common column values. For instance, a common column between two tables of parameter database 304 may include an identifier of a submission, such as a form entry, textual submission, accessory device tokens, local access addresses, metrics, and the like, for instance as defined herein; as a result, a search by a computing device 104 may be able to retrieve all rows from any table pertaining to a given submission or set thereof. Other columns may include any other category usable for organization or subdivision of data, including types of data, names and/or identifiers of individuals submitting the data, times of submission, and the like; persons skilled in the art, upon reviewing the entirety of this disclosure, will be aware of various ways in which data from one or more tables may be linked and/or related to data in one or more other tables.

Continuing in reference to FIG. 3, in a non-limiting embodiment, one or more tables of an parameter database 304 may include, as a non-limiting example, a biological extraction table 316, which may include categorized identifying data, as described above, including genetic data, epigenetic data, microbiome data, physiological data, and the like. Biological extraction table 316 may include biological extraction 112 categories according to parameter categories, may include linked tables to mathematical expressions that describe the impact of each biological extraction 112 datum on a parameter value. One or more tables may include nutrition parameter table 320, which may include data regarding nutrition parameter 116 value and numerical scale, a plurality of past nutrition parameters 116, data from alike subjects with similar nutrition parameters 116, and the like, that system 100 may use to calculate, derive, filter, retrieve and/or store nutrition parameters 116. One or more tables may include endurance parameter table 324, which may include data regarding endurance parameter 120 value and numerical scale, a plurality of past endurance parameters 120, data from alike subjects with similar endurance parameters 116, and the like, that system 100 may use to calculate, derive, filter, retrieve and/or store endurance parameters 116. One or more tables may include strength parameter table 328, which may include data regarding strength parameter 120 value and numerical scale, a plurality of past strength parameters 120, data from alike subjects with similar strength parameters 116, and the like, that system 100 may use to calculate, derive, filter, retrieve and/or store strength parameters 116. One of more tables may include a physical guidance table 332, which may include guidance instructions, numerical values, and/or outputs, determinations, variables, and the like, organized into subsets of data for generating instructions for nutrition programs, endurance training, strength training regimens, fitness programs, and the like. One or more tables may include, without limitation, a heuristic table 336, which may organize rankings, scores, models, outcomes, functions, numerical values, scales, arrays, matrices, and the like, that represent determinations, probabilities, metrics, parameters, and the like, include one or more inputs describing potential mathematical relationships, as described herein.

Figure 4:
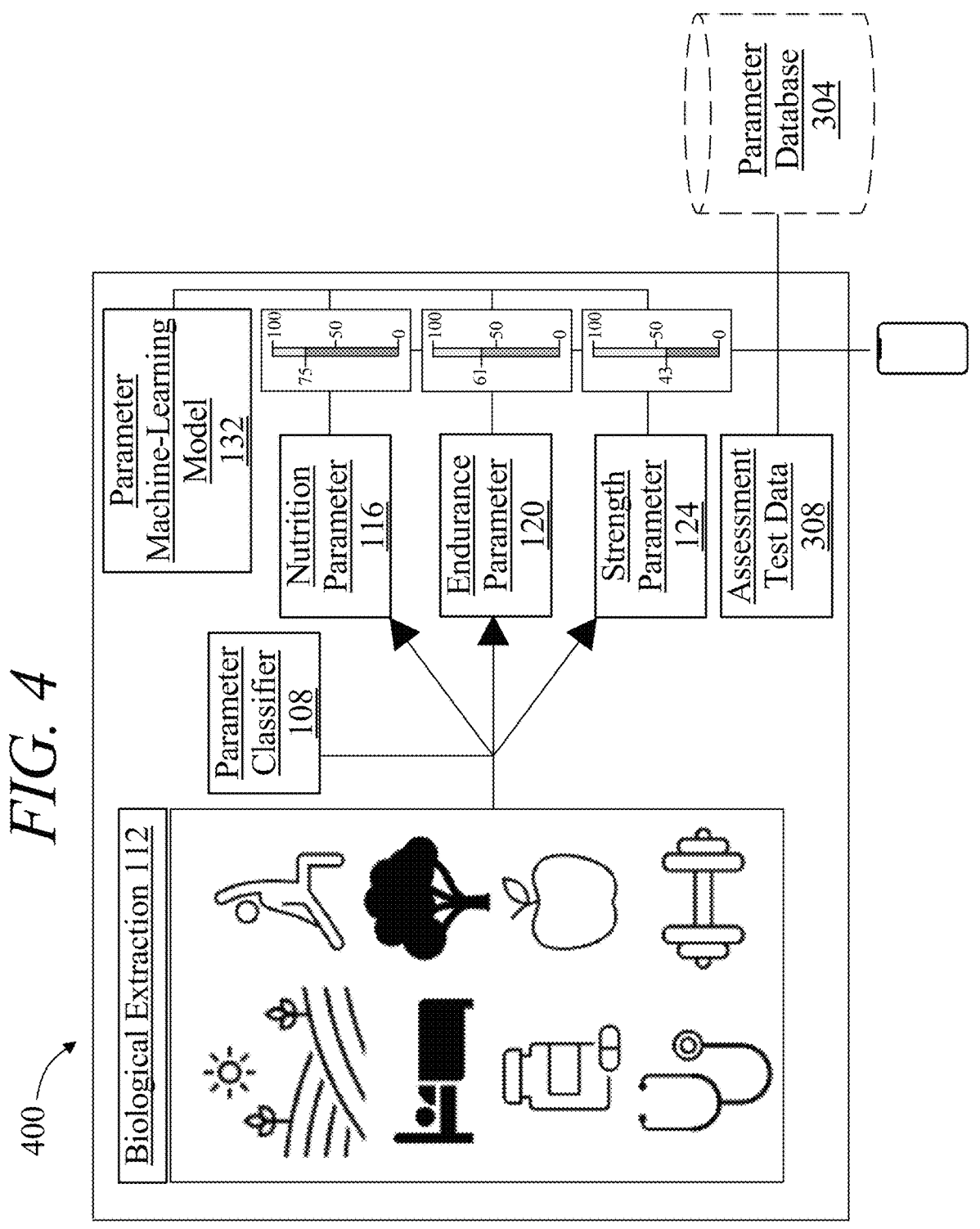
FIG. 4 is a diagrammatic representation of a non-limiting exemplary embodiment of a parameter classifier.

Referring now to FIG. 4, an exemplary embodiment 400 of a of a parameter classifier 108 is illustrated. Computing device 104 is configured to receive biological extraction 112. Biological extraction 112 may be stored and/or retrieved from a database, such as a parameter database 304. Biological extraction 112 may originator from subject or from a secondary source, such as a physician, laboratory technician, caretaker, etc. Biological extraction 112 may include a variety of data, from a variety of categories, such as fitness data, sleep quality data, nutrition input data, medical history, current supplements, medications, pharmacological agents, bioactive ingredients, diet, leisure activity, stress factors, mental health evaluations, among a variety of other biological extraction data 112. Parameter classifier 108 may categorize biological extraction to each parameter category. Biological extraction effect may be determined by parameter classifier 108, parameter machine-learning model 132, or any lazy-learning process 220, machine-learning model 224, supervised machine-learning process 228, unsupervised machine-learning process 323, or the like, as described herein.

Still referring to FIG. 4, parameter machine-learning model 132 may derive numerical scales for each parameter, as described above. Each parameter may be assigned a numerical value according to the model, machine-learning process, or the like, as described herein. Numerical value and scale, for instance and without limitation for nutrition parameter 116 may be derived as a function of '100 subcategories' of macronutrients, micronutrients, electrolytes, caloric intake, etc. as a function of the subjects, sex, age, fitness level, sleep quality, BMI, and the like, derived from nutritional input and biological extraction 112 by the parameter classifier 108. The value provided may be assigned by the trained parameter machine-learning model 132 using an algorithm that combines the nutritional deficiencies (chronic and acute from blood panel), nutritional surpluses (from nutritional inputs), caloric input (macro tracker), to provide a numerical value such as a score of '75' out of '100'. This may be performed for each category and for each biological extraction 112 datum that is classified to each class. Parameter values may be further refined against alike subjects. Assessment tests may be provided to 'test' the 'hypothesis' that a parameter value is accurate. Persons skilled in the art will appreciate the parameter values may be improved with larger biological extraction 112 datasets and with routine assessment test data.

Figure 5:
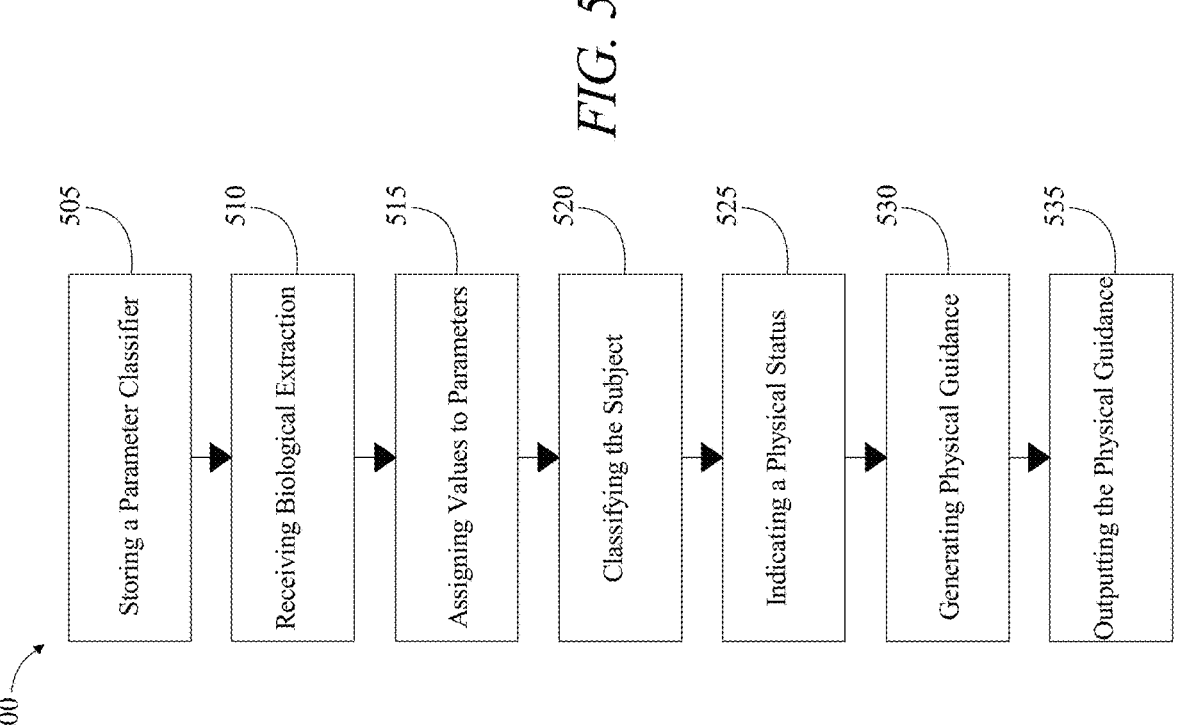
FIG. 5 is a block diagram of an exemplary workflow of a method for determining the physical status of a subject.

Referring now to FIG. 5, a non-limiting exemplary embodiment 500 of a method for determining the physical status of a subject is illustrated. At step 505, system 100 includes storing, by a computing device 104, a parameter classifier 108, the parameter classifier 108 configured to classify biological extraction 112 parameters to classes relating to nutrition, endurance, and strength of a subject. Prior to providing step it is determined whether the subject is suitable for being subject to the system 100. The parameter classifier 108 configured to classify physiological status parameters may include generating the parameter classifier 108 using a classification machine-learning process to categorize biological extraction 112 data to parameter classes; this may be implemented, without limitation, as described above in FIGS. 1-4.

Still referring to FIG. 5, at step 510, computing device 104 is configured for receiving, by the computing device, biological extraction 112 data of the subject; this may be implemented, without limitation, as described above in FIGS. 1-4.

Continuing in reference to FIG. 5, at step 515, computing device 104 is configured for assigning values to the parameters of the subject as a function of the biological extraction 112 data. A nutrition parameter 116 is assigned by determining a nutritional input of the subject. An endurance parameter 120 may be assigned by measuring the performance of an endurance test. A strength parameter 124 is assigned by measuring the performance of a strength test. Assigning values to the parameters may include training a parameter machine-learning model 132 with training data that includes a plurality of data entries wherein each data entry is correlated to a numerical scale for each parameter; this may be implemented, without limitation, as described above in FIGS. 1-4.

Continuing in reference to FIG. 5, at step 520, computing device 104 is configured for classifying the subject into classes as a function of each of the parameters; this may be implemented, without limitation, as described above in FIGS. 1-4.

Continuing in reference to FIG. 5, at step 525, computing device 104 is configured for indicating a physical status of the subject as a function of the classes; this may be implemented, without limitation, as described above in FIGS. 1-4.

Continuing in reference to FIG. 5, at step 530, computing device 104 is configured for generating physical guidance 136 for the subject as a function of the physical status. The steps of the method are repeated in defined intervals; this may be implemented, without limitation, as described above in FIGS. 1-4.

Continuing in reference to FIG. 5, at step 535, computing device 104 is configured for outputting the physical guidance 136. Outputting the physical guidance 136 may include generating a representation, via a graphical user interface, of the physical guidance 136. Outputting physical guidance 136 may include providing, to the subject, at least a wearable device identity associated with measuring the physical guidance 136; this may be implemented, without limitation, as described above in FIGS. 1-4.

It is to be noted that any one or more of the aspects and embodiments described herein may be conveniently implemented using one or more machines (e.g., one or more computing devices that are utilized as a subject computing device for an electronic document, one or more server devices, such as a document server, etc.) programmed according to the teachings of the present specification, as will be apparent to those of ordinary skill in the computer art. Appropriate software coding may readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 6:
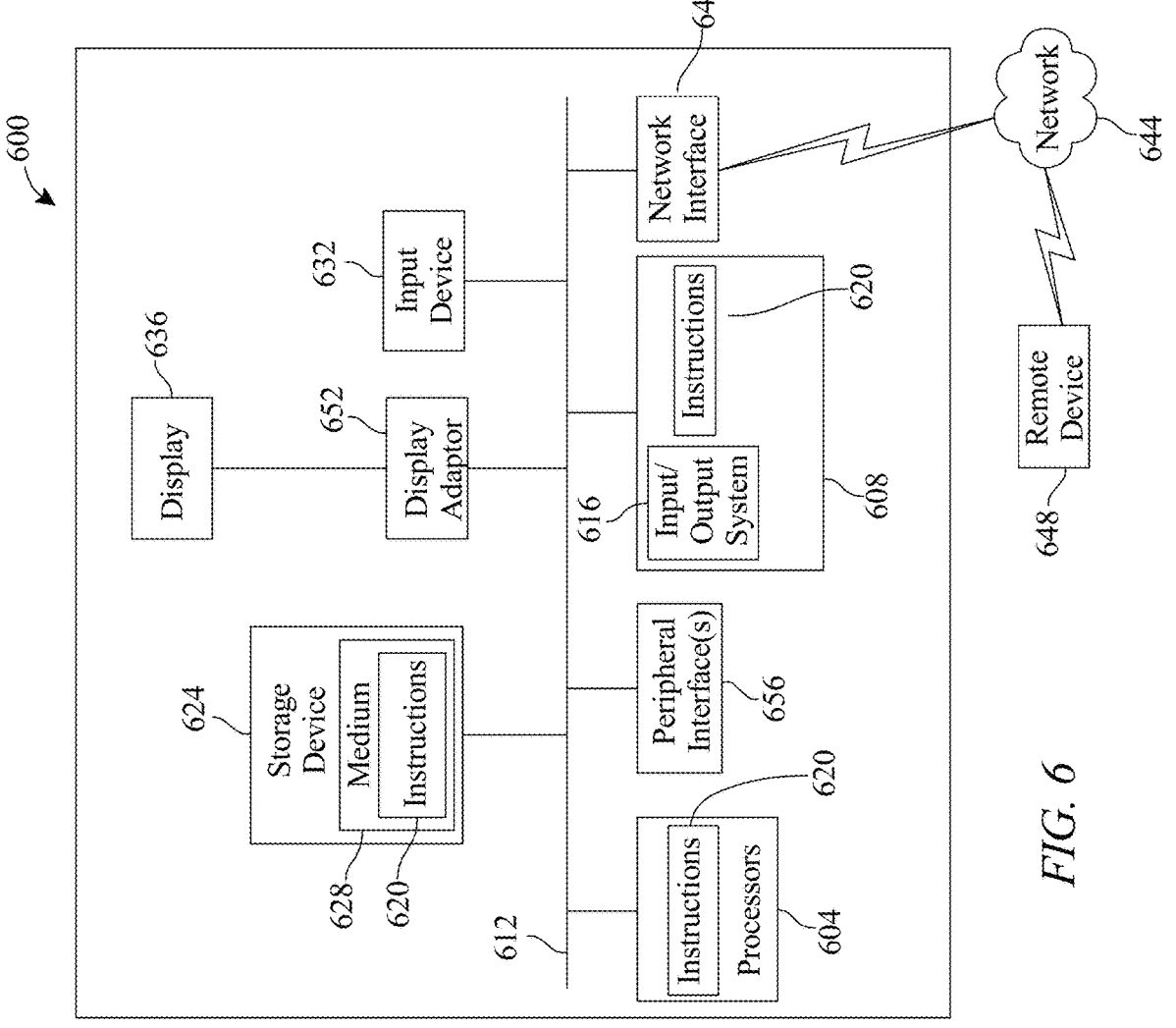
FIG. 6 is a block diagram of a computing system that may be used to implement any one or more of the methodologies disclosed herein and any one or more portions thereof.

FIG. 6 shows a diagrammatic representation of one embodiment of a computing device in the exemplary form of a computer system 600 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 600 includes a processor 604 and a memory 608 that communicate with each other, and with other components, via a bus 612. Bus 612 may include any of several types of bus structures including, but not limited to, a memory bus, a memory controller, a peripheral bus, a local bus, and any combinations thereof, using any of a variety of bus architectures.

Processor 604 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 604 may be organized according to Von Neumann and/or Harvard architecture as a non-limiting example. Processor 604 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC)

Memory 608 may include various components (e.g., machine-readable media) including, but not limited to, a random-access memory component, a read only component, and any combinations thereof. In one example, a basic input/output system 616 (BIOS), including basic routines that help to transfer information between elements within computer system 600, such as during start-up, may be stored in memory 608. Memory 608 may also include (e.g., stored on one or more machine-readable media) instructions (e.g., software) 620 embodying any one or more of the aspects and/or methodologies of the present disclosure. In another example, memory 608 may further include any number of program modules including, but not limited to, an operating system, one or more application programs, other program modules, program data, and any combinations thereof.

Computer system 600 may also include a storage device 624. Examples of a storage device (e.g., storage device 624) include, but are not limited to, a hard disk drive, a magnetic disk drive, an optical disc drive in combination with an optical medium, a solid-state memory device, and any combinations thereof. Storage device 624 may be connected to bus 612 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 624 (or one or more components thereof) may be removably interfaced with computer system 600 (e.g., via an external port connector (not shown)). Particularly, storage device 624 and an associated machine-readable medium 628 may provide nonvolatile and/or volatile storage of machine-readable instructions, data structures, program modules, and/or other data for computer system 600. In one example, software 620 may reside, completely or partially, within machine-readable medium 628. In another example, software 620 may reside, completely or partially, within processor 604.

Computer system 600 may also include an input device 632. In one example, a user of computer system 600 may enter commands and/or other information into computer system 600 via input device 632. Examples of an input device 632 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 632 may be interfaced to bus 612 via any of a variety of interfaces (not shown) including, but not limited to, a serial interface, a parallel interface, a game port, a USB interface, a FIRE-WIRE interface, a direct interface to bus 612, and any combinations thereof. Input device 632 may include a touch screen interface that may be a part of or separate from display 636, discussed further below. Input device 632 may be utilized as a user selection device for selecting one or more graphical representations in a graphical interface as described above.

A user may also input commands and/or other information to computer system 600 via storage device 624 (e.g., a removable disk drive, a flash drive, etc.) and/or network interface device 640. A network interface device, such as network interface device 640, may be utilized for connecting computer system 600 to one or more of a variety of networks, such as network 644, and one or more remote devices 648 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 644, may employ a wired and/or a wireless mode of communication. In general, any network topology may be used. Information (e.g., data, software 620, etc.) may be communicated to and/or from computer system 600 via network interface device 640.

Computer system 600 may further include a video display adapter 652 for communicating a displayable image to a display device, such as display device 636. Examples of a display device include, but are not limited to, a liquid crystal display (LCD), a cathode ray tube (CRT), a plasma display, a light emitting diode (LED) display, and any combinations thereof. Display adapter 652 and display device 636 may be utilized in combination with processor 604 to provide graphical representations of aspects of the present disclosure. In addition to a display device, computer system 600 may include one or more other peripheral output devices including, but not limited to, an audio speaker, a printer, and any combinations thereof. Such peripheral output devices may be connected to bus 612 via a peripheral interface 656. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions may be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions, and additions may be made to that which is specifically disclosed herein without departing from the spirit and scope of the present invention.

What is claimed is:

1. A system for determining a physical status of a subject, the system comprising:

a wearable device configured to record data, wherein the data comprises biological extraction data; and a computing device, the computing device configured to:

store a parameter classifier, the parameter classifier configured to classify biological extractions to physiological status parameters of subjects, wherein the physiological status parameters include a nutrition parameter which is assigned by determining a nutritional input of subjects, an endurance parameter comprising at least a physical endurance of subjects, and a strength parameter comprising at least a quantitative parameter describing strength of subjects and wherein the storing the parameter classifier further comprises generating the parameter classifier using a classification machine-learning model which comprises:

receiving training data, wherein the training data correlates a plurality of biological extraction data entries to a plurality of physiological status parameter categories, wherein receiving the training data comprises:

applying the training data to an input layer of nodes comprising the plurality of biological extraction data entries;

adjusting one or more connections and one or more weights between the input layer of nodes, one or more intermediate layers of nodes, and an output layer of nodes in adjacent layers of the classification machine-learning model, wherein the output layer of nodes comprises the plurality of physiological status parameter categories;

detecting additional correlations between the output layer of nodes and the input layer of nodes;

iteratively updating the classification machine-learning model as a function of the detected additional correlations;

training, iteratively, the classification machine-learning model using the training data, wherein training the classification machine-learning model includes retraining the classification machine-learning model with feedback from previous iterations of the classification machine-learning model;

classifying the plurality of biological extractions to the physiological parameters of subjects as a function of the trained classification machine-learning model;

receive the biological extraction data of a subject from the wearable device;

classify subject biological extraction to subject physiological parameters as a function of the stored parameter classifier;

determine threshold values for each subject physiological parameter of the subject physiological parameters as a function of the classification;

assign values to subject physiological status parameters as a function of the physiological parameters, wherein assigning values to the subject physiological status parameters are iterated as a function of defined intervals wherein the defined intervals are updated in real-time as a function of the data recorded from the wearable device;

determine a suitability of the subject using at least an assessment test, wherein determining the suitability of the subject comprises comparing each subject physiological status parameter assigned value to the threshold values, wherein the suitability of the assessment test is calculated as a numerical value wherein the numerical value is used to provide assessment test data for determining the subject physiological parameters;

indicate the physical status of the subject as a function of the subject physiological parameters and the suitability of the subject;

generate a physical guidance for the subject as a function of the physical status; and output the physical guidance.

2. The system of claim 1, wherein the storing the parameter classifier further comprises generating the parameter classifier using a classification machine-learning process to categorize biological extraction data to parameter classes.

3. The system of claim 1, wherein subject physiological parameters include an endurance parameter that is assigned by measuring a performance of an endurance test.

4. The system of claim 1, wherein subject physiological parameters include a strength parameter that is assigned by measuring a performance of a strength test.

5. The system of claim 1, wherein assigning values to the parameters further comprises:

training a parameter machine-learning model with training data that includes a plurality of data entries wherein each data entry is correlated to a numerical scale for each parameter; and assigning the values as a function of the parameter machine-learning model.

6. The system of claim 1, wherein providing the physical guidance further comprises generating a representation, via a graphical user interface, of the physical guidance.

7. The system of claim 1, wherein providing physical guidance further comprises providing, to the subject, at least a wearable device identity associated with measuring the physical guidance.

8. A method for determining a physical status of a subject, the method comprising:

recording data, by a wearable device, wherein the data comprises biological extraction data;

storing, by a computing device, a parameter classifier, the parameter classifier configured to classify biological extractions to physiological status parameters of subjects, wherein the physiological status parameters include a nutrition parameter which is assigned by determining a nutritional input of subjects, an endurance parameter comprising at least a physical endurance of subjects, and a strength parameter comprising at least a quantitative parameter describing strength of subjects and wherein the storing the parameter classifier further comprises generating the parameter classifier using a classification machine-learning model which comprises:

receiving training data, wherein the training data correlates a plurality of biological extraction data entries to a plurality of physiological status parameter categories, wherein receiving the training data comprises:

applying the training data to an input layer of nodes comprising the plurality of biological extraction data entries;

adjusting one or more connections and one or more weights between the input layer of nodes, one or more intermediate layers of nodes, and an output layer of nodes in adjacent layers of the classification machine-learning model, wherein the output layer of nodes comprises the plurality of physiological status parameter categories;

detecting additional correlations between the output layer of nodes and the input layer of nodes;

iteratively updating the classification machine-learning model as a function of the detected additional correlations;

training, iteratively, the classification machine learning-model using the training data, wherein training the classification machine-learning model includes retraining the classification machine-learning model with feedback from previous iterations of the classification machine-learning model;

classifying the plurality of biological extractions to the physiological parameters of subjects as a function of the trained classification machine-learning model;

receiving, by the computing device, the biological extraction data of a subject from the wearable device;

classifying, by the computing device, subject biological extraction to subject physiological parameters as a function of the stored parameter classifier;

determining, by the computing device, threshold values for each subject physiological parameter of the subject physiological parameters as a function of the classification;

assigning, by the computing device, values to subject physiological status parameters as a function of the biological extraction data, wherein assigning values to the subject physiological status parameters are iterated as a function of defined intervals wherein the defined intervals are updated in real-time as a function of the data recorded from the wearable device;

determining, by the computing device, a suitability of the subject using at least an assessment test, wherein determining the suitability of the subject comprises comparing each subject physiological status parameter assigned value to the threshold values, wherein the suitability of the assessment test is calculated as a numerical value wherein the numerical value is used to provide assessment test data for determining the subject physiological parameters;;

indicating, by the computing device, the physical status of the subject as a function of the subject physiological parameters and the suitability of the subject;

generating, by the computing device, a physical guidance for the subject as a function of the physical status; and outputting, by the computing device, the physical guidance.

9. The method of claim 8, wherein the storing the parameter classifier further comprises generating the parameter classifier using a classification machine-learning process to categorize biological extraction data to parameter classes.

10. The method of claim 8, wherein subject physiological parameters include an endurance parameter that is assigned by measuring a performance of an endurance test.

11. The method of claim 8, wherein subject physiological parameters include a strength parameter that is assigned by measuring a performance of a strength test.

12. The method of claim 8, wherein assigning values to the parameters further comprises:

training a parameter machine-learning model with training data that includes a plurality of data entries wherein each data entry is correlated to a numerical scale for each parameter; and assigning the values as a function of the parameter machine-learning model.

13. The method of claim 8, wherein providing the physical guidance further comprises generating a representation, via a graphical user interface, of the physical guidance.

14. The method of claim 8, wherein providing physical guidance further comprises providing, to the subject, at least a wearable device identity associated with measuring the physical guidance.

\* \* \* \* \*